(12) United States Patent
Huddleston

(10) Patent No.: US 8,245,845 B1
(45) Date of Patent: Aug. 21, 2012

(54) DISPOSABLE HOLDER AND CLEANER APPARATUS FOR SURGICAL INSTRUMENTS, HOSES, CABLES AND THE LIKE

(76) Inventor: Herbert D. Huddleston, Encino, CA (US)

( * ) Notice: Subject to any disclaimer, the term of this patent is extended or adjusted under 35 U.S.C. 154(b) by 1599 days.

(21) Appl. No.: 11/634,469

(22) Filed: Dec. 6, 2006

(51) Int. Cl.
*B65D 83/10* (2006.01)
(52) U.S. Cl. ...................... 206/363; 15/218.1
(58) Field of Classification Search ............. 206/363, 206/370, 484; 15/218.1; 451/461, 463, 464, 451/486
See application file for complete search history.

(56) References Cited

U.S. PATENT DOCUMENTS

| | | | |
|---|---|---|---|
| 3,128,072 A | 4/1964 | Shibata | |
| 3,696,920 A | 10/1972 | Lahay | |
| 3,982,357 A | 9/1976 | Eldridge et al. | |
| 4,074,397 A | 2/1978 | Rosin | |
| 4,174,816 A | 11/1979 | Olson | |
| 4,417,710 A | 11/1983 | Adair | |
| 4,793,483 A | 12/1988 | Holmes | |
| 5,102,399 A | 4/1992 | Chu | |
| 5,160,106 A | 11/1992 | Monick | |
| 5,334,186 A | 8/1994 | Alexander | |
| 5,533,618 A | 7/1996 | Pickles, Jr. | |
| 6,021,540 A | 2/2000 | Miller et al. | |
| 6,431,500 B1 | 8/2002 | Jacobs et al. | |
| 6,575,298 B1 | 6/2003 | McArthur et al. | |

*Primary Examiner* — Melanie Hand
(74) *Attorney, Agent, or Firm* — Thomas I. Rozsa

(57) ABSTRACT

A disposable surgical instrument apparatus that has a generally rectangular shaped holder body with one or more elongated cylinders for retaining a plurality of surgical instruments, such as a suction device, a cautery and other instruments when not in use during surgery. One of the cylinders has a sealed chamber with a passageway that progressively decreases in diameter to accommodate a plurality of different size suction nozzle of the suction device within the chamber. One or more slotted channels are respectively associated with the cylinders for retaining hoses and electrical wires of the surgical instruments. The apparatus has a cleaning spike for de-clogging the suction nozzle of the suction device. The apparatus further has an abrasive pad for scraping char off the tip of the cautery.

11 Claims, 9 Drawing Sheets

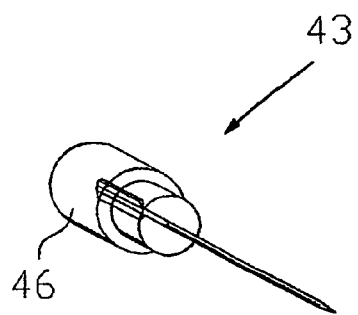
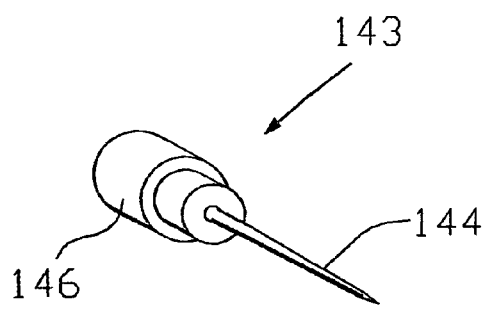
Fig. 9A
Fig. 9B
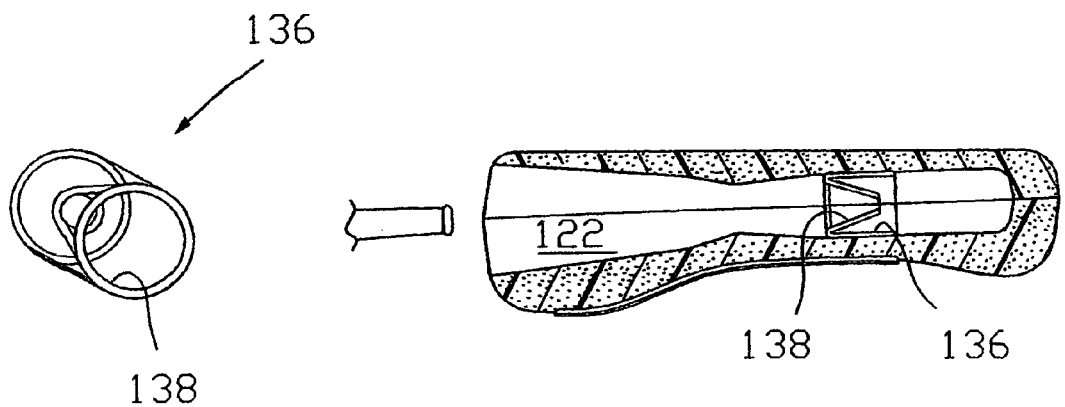
Fig. 10A
Fig. 10B

DISPOSABLE HOLDER AND CLEANER APPARATUS FOR SURGICAL INSTRUMENTS, HOSES, CABLES AND THE LIKE

BACKGROUND OF THE INVENTION

1. Field of the Invention

The present invention relates generally to the field of surgical instruments. More particularly, the present invention relates to the field of surgical instrument apparatuses for holding and cleaning a plurality of surgical instruments used together in a surgery, such as a cautery, a suction device or the like, when not in use and for holding the tube and/or cord attached to the surgical instrument in a predetermined location but permitting movement in response to the surgeon pulling the surgical instrument.

2. Description of the Prior Art

A flexible suction hose is usually used for evacuating blood or other fluids from the surgical wound-cavity during operations on humans or animals. One end of the suction hose is attached to a continuous negative-pressure source located a few feet away from the operating table and sterile operating field. The surgeon's end of the sterile hose is usually fitted with a rigid suction nozzle which is available in different sizes and shapes.

The suction hose is usually anchored to a convenient location on the sterile drapes, such that a loop of the suction hose is formed between the anchorage and the nozzle. The length of the loop of the hose can be adjusted to allow easy reach of the suction tip to all parts of the wound. The hose is usually anchored by wrapping two folds of the sterile drapes around the hose and clamping the folds together with a stainless steel surgical clamp (i.e., Alice clamp, towel clip and etc.). Alternatively, the surgical clamp is attached directly to the drapes and the hose is threaded through one or both finger holes of the clamp handles.

When the suction nozzle is not in use, the suction nozzle is placed on the drapes over the patient, or is placed in a scabbard comprised of an elongated metal or plastic tube container which is closed at one end, or a flat, soft-plastic pocket or sheath, either of which is attached to the sterile drapes by means of a surgical clamp or by adhesive backing.

Suction is provided continuously precluding the need for the surgeon to actuate valves, operate switches and/or the like.

This overall prior art arrangement has many disadvantages. The upper surfaces of the drapes are irregularly convex surfaces and do not provide a secure storage space. The loop of the hose and its nozzle, and other instruments, such as the cautery and its cable, that are placed on this surface have a constant gravitational tendency to slide off onto the floor where they become contaminated and have to be replaced.

Further, although the surgeon may set the loop of tubing and its nozzle down at a point on the drapes that seems secure, the hose is unruly and does not readily remain where it is placed. The hose has a tendency to spring to a different location determined by the stiffness, springiness and other physical characteristics of plastic hose, as well as by the nature and orientation of the hose anchorage. It may thus spring to a less secure location from where it may fall to the floor or it may spring to a location where the surgeon may not readily locate it without taking his or her eyes off the operation.

A hard plastic or metal scabbard, if used is usually anchored to the sterile drapes with a towel clip or other clamp passed through a hole or loop near its upper end. The towel clip often doubles as an anchorage for the vacuum hose by threading the hose through the clamp's finger holes. This provides no control over the direction in which the anchored hose will lie. Also, the nozzle is frequently sprung from the scabbard by the springy properties of the loop of plastic tubing. Also, being anchored only at its upper end, the scabbard is unstable and prone to being upended by the weight of the tubing, thereby causing its contents to be dumped onto the floor. Also, when the nozzle is in the scabbard, a stiff loop of hose between the nozzle and anchor site often protrudes vertically well above the scabbard, where it may get contaminated against the surgeon's mask or otherwise obtrude into the surgeons work space.

If a towel clip or other clamp-like instrument is used to anchor the scabbard or the suction tubing, it can penetrate or tear the sterile drapes. A plastic pocket with a pressure-sensitive adhesive backing is commercially available for housing the suction nozzle, but its adhesive usually does not stick well to the drapes, it is usually too shallow and inserting the nozzle into a flat, collapsed pocket can be somewhat cumbersome.

The surgeon and his team are thus constantly distracted by concern over the hose and nozzle sliding off onto the floor or obtruding into the surgical area or by having to locate the nozzle when needed.

If the hose or nozzle does fall to the floor, the operation has to be interrupted while it is replaced, unnecessarily prolonging the operating and anesthesia time. An attendant may have to leave the operating room to find replacements. The tubing has to be detached from its anchorage and from the vacuum source, and the new tubing and nozzle have to be connected and anchored. The attachment and detachment of the anchoring clamp increases the risk of tearing the drapes and contaminating the sterile field. The lost time and the cost of replaced instruments are additional to the cost of the operation.

The provision of continuous suction without the ability to easily shut-off when not in use has several disadvantages. The suction nozzle creates a continuous, objectionable hissing noise which is distracting and makes for an uncomfortable workplace. Any hard, tube-like scabbard usually amplifies the objectionable sound. Operating room personnel frequently stop the noise by folding the suction hose on itself into a tight loop, thereby closing off the lumen of the hose and jamming the loop into any available suitable space. Alternately, a surgical clamp (hemostat, etc.) is used to clamp off the tubing.

Either method stops the hissing sound, but it takes a two-handed technique to remove the clamp, refold the tube and re-apply the clamp. Also, a clamp adds weight to the tubing rendering it even more likely to upend an unstable scabbard. Suction nozzles are available with a finger-operated on-off valve, but they are inconvenient and are almost never used.

Another problem with prior art, there are residual bacteria in the room air of even the cleanest of operating rooms. The continuous negative pressure of the suction hose, draws a constant flow of room air to and through the tip of the nozzle. The nozzle is frequently dipped into, and it is therefore constantly coated by, blood and other body fluids, which form a sticky bacterial culture medium on the nozzle tip to which bacteria from the constantly flowing air can adhere. These bacteria can be a source of wound infection, either directly when the suction nozzle is reintroduced into the wound or, indirectly when the suction nozzle is housed in the same container as other instruments and comes into direct contact with such other instruments. Having means to easily shut off the suction nozzle when it is not in use would thus decrease the chances of wound infections.

Another problem with prior art is that the suction hose is usually connected via a series of canisters to other suction hoses in use in the same operating room, either to add suction lines used by the surgeon or to a separate suction line used by the anesthesiologist for suctioning secretions from the patient's throat. When multiple hoses are in use in the same operating room, they siphon off negative vacuum pressure from each other, mutually decreasing the suction efficiency of all the lines in use.

The vacuum lines from each operating room in a suite of multiple operating rooms are usually interconnected via a central vacuum pipe connected to a central vacuum pump. The negative pressure lost through any open vacuum hose reduces the strength of the vacuum to other vacuum hoses in the same operating room or in other operating rooms fed by the same system. Occluding suction hoses that are not in actual use therefore increases the general efficiency of the suction system in the entire operating room suite.

A further problem with prior art devices is that the tip of the suction nozzle frequently becomes clogged with soft tissue or bone fragments. The surgeon has to pry the blockage with a long narrow needle-like instrument to dislodge the blockage. Most often the tip of the cautery is used, but it is usually too short or too thin, and the tine of a hemostat is usually too thick, short and curved for dislodging the blockage. In addition, both methods require two hands to perform the dislodging maneuver.

The pencil-like cautery and its flexible cable share many of the problems encountered with the suction hose and its suction nozzle. Its cable must have anchorage, and the device and its loop of cable are also often laid on the drapes over the patient, thereby having a similar tendency to fall to the floor. Many suppliers package it with a small hard-plastic scabbard which is clamped to the drapes with a towel clip, rendering the scabbard unstable as noted above.

A flat soft plastic pocket is commercially available. It is secured to the drapes by a pressure-sensitive adhesive. The main disadvantage is that its thin wall and hence the underlying drapes are susceptible to penetration by the sharp tip of the cautery, with the potential for contamination or injury to the patient's underlying skin by sharp penetration, electric or thermal injury. The pocket is usually in a collapsed state which can make insertion of an instrument cumbersome.

Frequently, the scabbard used for the suction nozzle doubles as a holder for the cautery, where the suction hose and cautery line frequently become entangled. The close proximity of the two instruments increases the risk of bacterial cross-contamination and the combined weight adds to the tendency for the scabbard to upend, dropping both the instruments on the floor. For these reasons it is desirable to have separate holders for the cautery and the suction nozzle.

The cautery has an additional problem in that its flat, paddle-like metal electrode often becomes caked with charred tissue rendering it less conductive and therefore less efficient. A small swatch of abrasive paper is commercially available for cleaning the tip. It is applied to the surgical drapes by means of an adhesive backing. These swatches have the disadvantage of being flat so that only the tip of the electrode can be cleaned unless the surgeon takes the two-handed method of bending the electrode to an angle to present a flat surface parallel the flat swatch and then having to bend the electrode in the opposite direction to clean its other side in a similar manner and then having to straighten out the bent electrode.

Surgeons repeatedly use many other surgical instruments. These surgical instruments are often placed on the irregular upper surfaces of the drapes which cover the patient. Some of these surgical instruments are expensive and fragile and some have attached fiber-optic or electrical cables. Therefore, some means is required for securing and reliable retention of these instruments, as well as for anchorage their fiber-optic cable or other extensions.

U.S. Pat. No. 3,128,072 issued to Shibata on Apr. 7, 1964 discloses an article attaching device which includes a back member. The back member comprises a film of a flexible synthetic resin and a back surface which is coated with an adhesive agent. The adhesive surface is applied with an easily removable separator such as paper coated with a parting agent or cellophane.

U.S. Pat. No. 3,696,920 issued to Lahay on Oct. 10, 1972 discloses a device for organizing objects. It comprises a block of a semi-rigid foam which has a plurality of channels of a configuration adapted to retain the object therein, a beveled slot providing communication between the surface of the block and the channel, the width of the slot narrowing as it approaches the channel, and means for adhesively securing an outer surface of the block to a suitable supporting surface. The object is inserted through the beveled slot into the channel where it is retained in a locked position until needed. The object is then removed for use from the channel by expanding the slot sufficiently to permit the object to be withdrawn from the channel through the slot. The device only anchors tubes, cables or cords and provides no directionality to the secured object.

U.S. Pat. No. 4,074,397 issued to Rosin on Feb. 21, 1978 discloses a disposable device for securing cords, tubes, and the like during surgical or other medical operations. The device may be fastened to the paper or fabric sheet which covers the patient during surgery. The device comprises a thin, flexible pad that has a pressure-sensitive adhesive layer on one side so that it may be removably attached to the aforesaid sheet. It also has an elongated flexible strip portion integral with the pad. The strip portion is wrapped around the cord or tube to be secured by the device and anchored by a VELCRO®. The device only anchors tubes, cables or cords and provides no directionality to the secured object.

U.S. Pat. No. 4,174,816 issued to Olson on Nov. 20, 1979 discloses a sterile surgical cord and tube retractor. The device includes a housing adapted to be supported on the instrument table positioned adjacent the surgical filed. A plurality of spring-tensioned retractors within the housing separately hold lengths of tubing and cord, permitting them to be withdrawn from the housing for use and then retracted back into the housing.

U.S. Pat. No. 4,417,710 issued to Adair on Nov. 29, 1983 discloses a combined surgical instrument and tube holder device. The device is provided for yieldably supporting a hose and/or cord extending from a surgical instrument. The device includes a pad which is adhesively securable to a surgical drape or other surface and is connected to a releasable hose holding means by a stretchable member. The hose holding means includes a strip having a foam layer on one side and a fabric layer of intertwining material on the other side and a tab attached to one end of the strip and having an interlocking surface which releasably adheres to the fabric layer so as to hold the hose and/or cord in desired location while allowing them to move in response to movement of the surgical instrument. In one embodiment, the outer side of the pad has a layer of intertwining material and a strip of interlacing material is adhesively attached to the surgical instrument so that the instrument can be nested on the pad by pressing the interlacing material against the intertwining material on the pad.

U.S. Pat. No. 4,793,483 issued to Holmes on Dec. 27, 1988 discloses a tray for surgical patties. The tray is made of metal and is held to the drapes by means of alligator clips. Holders on the outer edges of the tray are provided for holding an electric cautery, cutter and forceps.

U.S. Pat. No. 5,102,399 issued to Chu on Apr. 7, 1992 discloses a clinical tube holder valve assembly and method. The holder assembly has a tube-receiving passage attached to a mounting block and a pressure-sensitive adhesive thereon for selectively mounting the suction tube holder. A portion of the fluid-flow tube is selectively folded on itself and inserted into the tube-receiving passage for being held therein at a fixed location with a blocked lumen.

U.S. Pat. No. 5,160,106 issued to Monick on Nov. 3, 1992 discloses an adaptor for anesthesia equipment. The apparatus comprises a support member for suction tubing and a catheter, means for clamping the support member to the operating room table and a passageway through the support member for receiving one end of the suction tubing. A catheter is provided which has one end for insertion in the patient's mouth and the other end for connection to one end of the suction tubing. Connection means is provided with one end of the suction tubing for preventing the catheter from passing through the passageway. The passageway is constructed and arranged so that the tubing can be pulled up through the support member to permit the catheter to reach the mouth of the patient and when released will slide back down and stop at the catheter so as to be readily available for reuse. A clamp is carried by the support member for clamping and unclamping the suction tubing and for controlling the suction through the suction tubing to the catheter. The support member has a portion which is shaped to receive a bar on the operating room table and means for clamping the support member to the operating room table. The clamping means comprises a screw member threadedly carried by the support member and one end adapted to engage the bar. The passageway through the support member includes a wall structure which provides low friction with respect to the suction tubing to be pulled therethrough. The passageway through the support member includes a tubular sleeve which has an inner surface for providing low friction with respect to the suction tubing when pulled therethrough.

U.S. Pat. No. 5,334,186 issued to Alexander on Aug. 2, 1994 discloses medical tubing and implement organizer. It allows medical implements to be held in a convenient location proximate to a patient and also allows the medical tubes to be organized and ordered according to size. The tubes are in generally cylindrical lateral bores.

U.S. Pat. No. 5,533,618 issued to Pickels, Jr. on Jul. 9, 1996 discloses a surgical holster for organizing hoses. The hoses are held in generally cylindrical lateral bores in the tubing holder. The hose holding portion of the device is demountably attached to the flat base portion.

U.S. Pat. No. 6,431,500 issued to Jacobs et al. on Aug. 13, 2002 discloses a flexible tube or cord anchoring apparatus which includes a base and a securement member. A cover is attachable at the base and includes a raised shield section which has an access opening. A mounting material layer is affixed at an opposite surface of the base for selected location and securement of the apparatus. In use, the hose or cord is releasably receivable at the securement member through the access opening at the shield section of the cover, where the securement member and the hose or cord received therein being recessed relative to the shield section.

U.S. Pat. No. 6,575,298 issued to McArthur et al. on Jun. 10, 2003 discloses a surgical instrument holder which includes a holder body with connecting adjacent elongated cylinders. The cylinders are able to hold a plurality of surgical instruments such as a diathermy pencil and suction means, or two laparoscopic instruments or the like, and allow easy removal of the instruments.

U.S. Pat. No. 3,982,357 issued to Eldridge et al. on Sep. 28, 1976 discloses a cleaning device for cautery. It includes a supporting frame adapted to be attached to a towel or drape used in surgery and held by an atraumatic clip. The frame has a pair of abrasive strips having mutually engaging surfaces provided with diverging entrance ends for a cauterizing knife to be inserted thereto.

U.S. Pat. No. 6,021,540 issued to Miller et al. on Feb. 8, 2000 discloses a tip cleaner for operating room instruments. It includes a base, upstanding bristles, at least one sharp vertical edge and a flat top.

It is highly desirable to have a very efficient and also very effective design and construction of a disposable surgical holder and cleaner apparatus which can securely retain surgical instruments when not in use during surgery, but allow easy removal of surgical instruments when they are required during surgery. In addition, the apparatus also provides means for easily shutting off the suction nozzle when not in use, de-clogging the tip of the suction nozzle as needed and scraping char off the tip of the cautery instrument, all with a one-handed technique.

SUMMARY OF THE INVENTION

The present invention is a disposable surgical instrument holder and cleaner apparatus which can securely retain a plurality of surgical instruments, such as a suction device, a cautery and other instruments when not in use during surgery. What is provided by the present invention is a secure, sterile, lightweight, flame-retardant, non-conducting, non-toxic device, which converts the generally irregular, generally convex, unusable, unstable surface over a draped surgical patient into usable, stable, working space.

The surgical instrument apparatus comprises a generally rectangular shaped body made from a semi-rigid foam or other suitable material which has one or more elongated cylinders for retaining a plurality of surgical instruments when not in use during surgery. The foam walls of the apparatus provide physical, electrical and thermal insulation from the patient. One of the elongated cylinders has means for shutting off the suction nozzle of the suction device when not in use. The means includes a sealed airtight chamber with a passageway which decreases in diameter to accommodate different sizes of suction nozzle, for gripping the suction nozzle, and shutting off the flow of negative pressure vacuum when the suction nozzle is not in use. One or more elongated slotted channels are respectively associated with the elongated cylinders, for retaining hoses and electrical wires of the surgical instruments. These slotted channels are angled to force direction on the hoses and electrical wires of the surgical instruments. The rectangular body of the apparatus has a conformed bottom surface for conforming to an irregular support surface. The apparatus further has an elongated cleaning spike or pin for de-clogging the suction nozzle of the suction device. The apparatus further has an abrasive pad for scraping char off the tip of the cautery.

An alternative shut-off means can be accomplished with provision of conical cavity, wide at its mouth and progressively narrower so that a narrow nozzle will find anchorage at a deep level and a wider nozzle will meet resistance and anchorage at a lesser depth. Second means is by the provision of two or more diaphragms located along the length of the cylinder. Each diaphragm has a hole for the passage of the suction nozzle and progressively decreases in diameter to accommodate different sizes of suction nozzle of the suction device.

It is an object of the present invention to provide a surgical instrument apparatus that overcomes the problems of the prior art but allows easy removal of a plurality of surgical instruments for surgical procedures.

It is also an object of the present invention to provide a surgical instrument apparatus which can securely hold the surgical instruments used in surgery that are needed to be in close proximity to the surgeon, some of which surgical instruments are attached to a fiber-optic cable, hose or electrical cord.

It is an additional object of the present invention to provide a surgical instrument apparatus that is disposable.

It is a further object of the present invention to provide a surgical instrument apparatus that has means for accommodating different diameters of a suction nozzle of a suction device and provides secure housing for the suction nozzle of the suction device, the cautery and other surgical instruments.

It is a further object of the present invention to provide a surgical instrument apparatus that has means for easily shutting off the suction nozzle of the suction device when not in use.

It is a further object of the present invention to provide a surgical instrument apparatus that has means for de-clogging the tip of the suction nozzle as needed.

It is a further object of the present invention to provide a surgical instrument apparatus that has means for scraping char off the tip of the cautery.

It is still a further object of the present invention to provide a surgical instrument apparatus that conforms to the irregular, generally convex surface of a patient's body converting it into a flat or concave surface for securely holding a plurality of surgical instruments.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 9A is a perspective view of a cleaning spike in accordance with the present invention;

FIG. 9B is a perspective view of another cleaning spike in accordance with the present invention;

FIG. 10A is a perspective view of a diaphragm in accordance with the present invention;

FIG. 10B is an alternative embodiment of FIG. 4 with the diaphragm inserted within the suction cylinder of the present invention;

DETAILED DESCRIPTION OF THE PREFERRED EMBODIMENTS

In the following description of the preferred embodiment, reference is made to the accompanying drawings which form a part hereof, and in which is shown by way of illustration a specific embodiment in which the present invention may be practiced. It is to be understood that other embodiments may be utilized and structural changes may be made without departing from the scope of the present invention.

Figure 1:
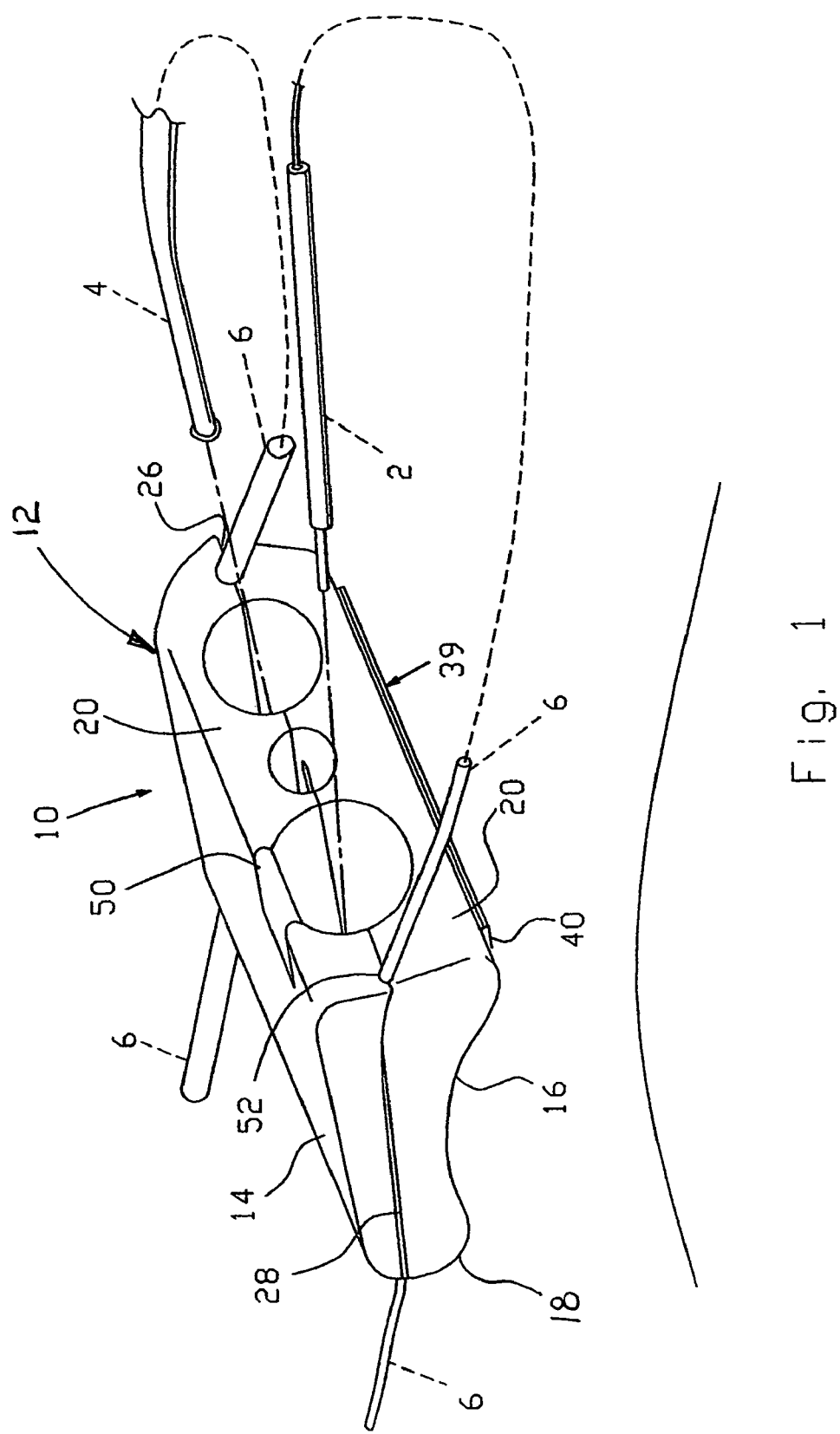
FIG. 1 is a perspective view of the present invention disposable surgical instrument apparatus for cleaning and holding surgical instruments, hoses and electrical cords.
Figure 8:
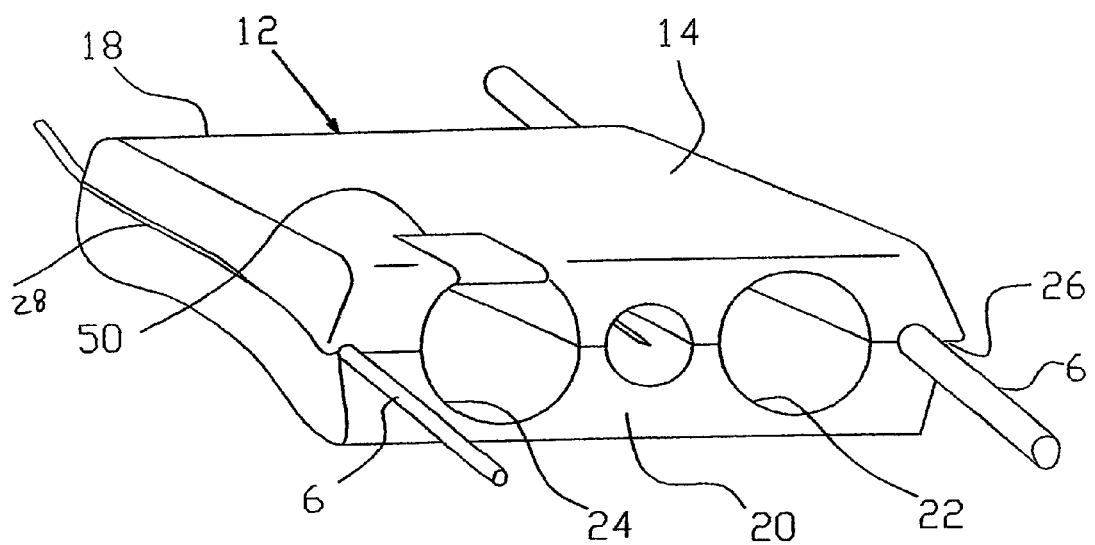
FIG. 8 is a top perspective view of the disposable surgical instrument apparatus of the present invention shown in FIG. 1.

Referring to FIGS. 1 and 8, there is shown the present invention disposable surgical instrument holder and cleaner apparatus referred to generally by the reference numeral 10. The holder and cleaner apparatus 10 can securely retain surgical instruments 2 and 4 when not in use during surgery. The apparatus 10 comprises a generally rectangular shaped holder body 12 which has a top surface 14, a contoured bottom surface 16, a thin rear end 18, a thick common end 20, one or more longitudinal elongated cylinders 22 and 24 disposed adjacent one another, and one or more elongated open slotted channels 26 and 28 respectively located adjacent to the elongated cylinders 22 and 24.

The object of the present invention is a surgeon workstation which can securely hold a plurality of surgical instruments, such as a suction device 4 and its suction hose 6, a cautery 2 and its electrical cord 8 or other surgical instruments (e.g., a diathermy pencil and laparoscopy instruments) used in surgery that are needed to be in close proximity to the surgeon, some of which the surgical instruments are attached to a fiber-optic cable, hose or electrical cord (hereafter referred to as "extensions").

Figure 4:
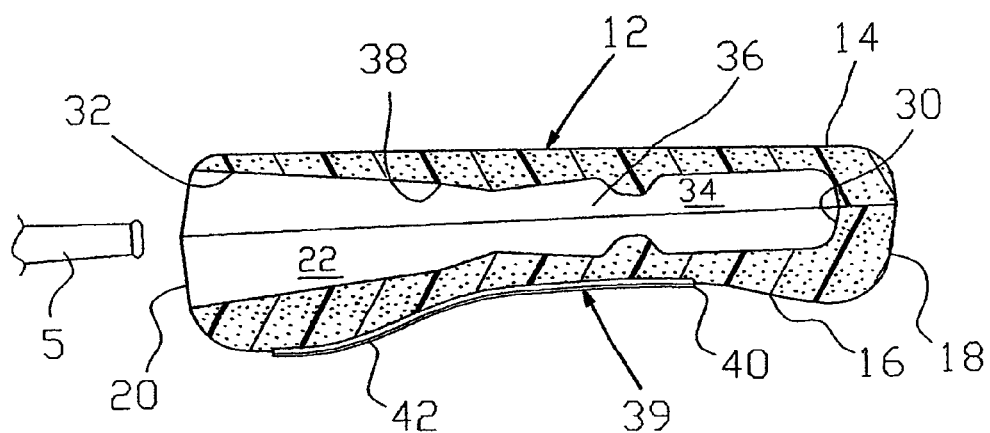
FIG. 4 is a cross-sectional view taken along line 4-4 of FIG. 2.
Figure 6:
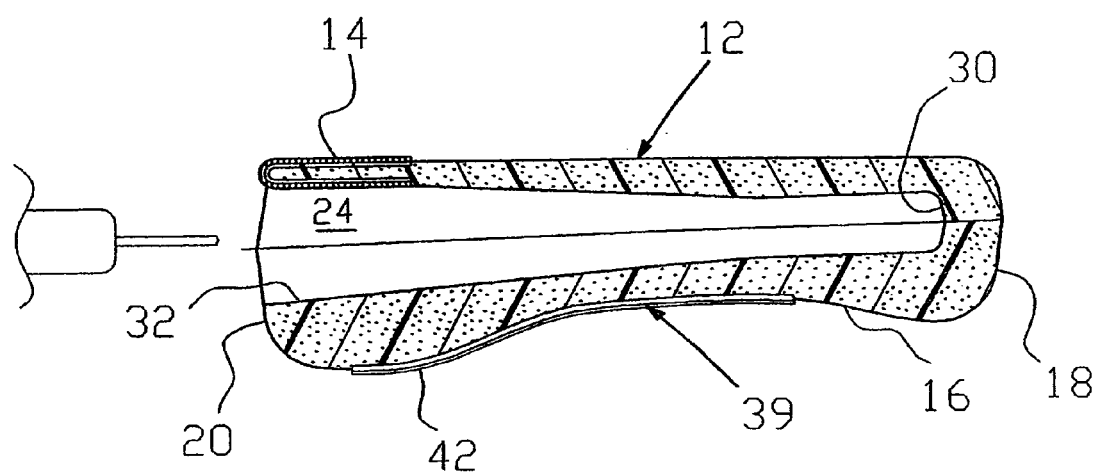
FIG. 6 is a cross-sectional view taken along line 6-6 of FIG. 2.

Referring to FIGS. 1, 4 and 6, each elongated cylinder has a closed end 30 and a conical open end 32 located at the thick common end 20 of the holder body 12 for ease of insertion of the surgical instruments and sized to hold the surgical instruments when not in use during surgery, but allow easy removal and replacement of the surgical instruments, such as a suction device 4, a diathermy pencil, laparoscopic instruments or the like. The elongated suction cylinder 22 provides means for easily and automatically shutting off the suction nozzle 5 of the suction device 4 when not in use and eliminating the objectionable noise from the suction nozzle 5 of the suction device 4. The shut-off means has a sealed airtight chamber 34 with a passageway 36 that decreases in diameter 38 for accommodating a plurality of different sized suction nozzles, where the sealed airtight chamber 34 stops the suction action and muffles the noise from the suction nozzle 5 of the suction device 4. The passageway 36 of the elongated cylinder 22 is contoured so as to accept and seal suction nozzles of different sizes and shapes. The passageway 36 of the cylinder 22 has a smaller diameter than the diameter of the suction nozzle 5 for insertion of the suction nozzle, such that the suction nozzle can be securely held and at the same time be sealed without the need for a diaphragm. The passageway 36 is progressively narrower so that a narrow suction nozzle will find anchorage at a deeper level of the cylinder 22 and a wider suction nozzle will meet resistance and anchorage at a lesser depth of the cylinder 22. The elongated cautery cylinder 24 securely holds the cautery or the like in place when not in use during surgery, but allows easy removal and replacement of the cautery. The two separate elongated cylinders 22 and 24 decrease the possible airborne contaminations of the nozzle tip. The longitudinal elongated cylinder 24 can also be made by having the cylinder 24 extend through the entire body 12 with openings at both ends to accommodate a longer surgical instrument thereto.

Referring to FIGS. 10A and 10B, there is shown an alternative embodiment of the suction cylinder 122 of the present invention holder and cleaner apparatus.

Alternatively, a diaphragm or insert 136 can be inserted along the length of the suction cylinder 122, where the diaphragm 136 has an opening 138 for the passage of the suction nozzle of a suction device. The hole 138 has a progressively smaller diameter to accommodate different sized suction nozzles.

Figure 3:
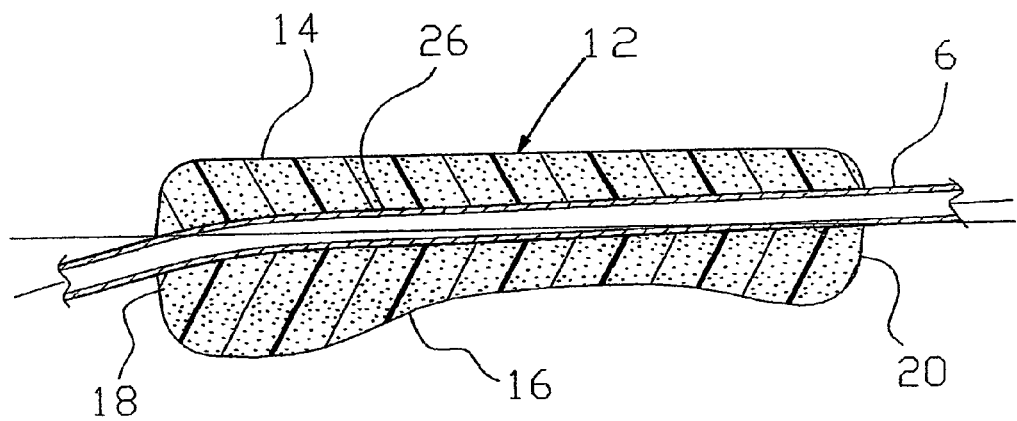
FIG. 3 is a cross-sectional view taken along line 3-3 of FIG. 2.
Figure 7:
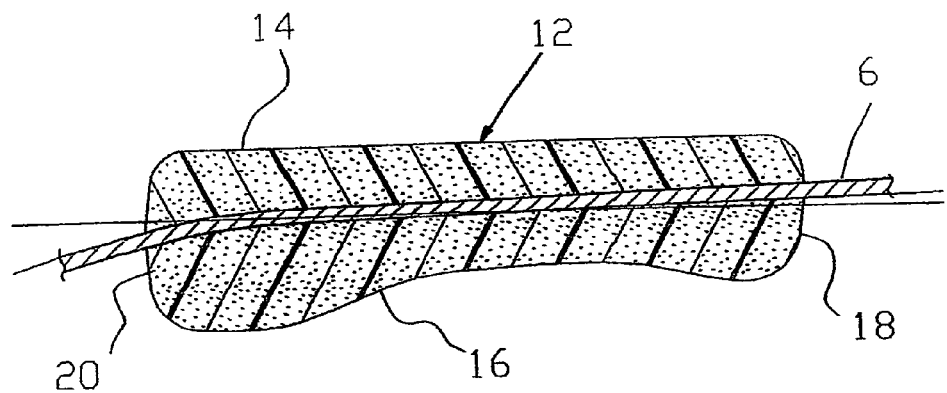
FIG. 7 is a cross-sectional view taken along line 7-7 of FIG. 2.

Referring to FIGS. 3, 7 and 8, the two elongated open slotted channels 26 and 28 are respectively located adjacent to the elongated cylinders 22 and 24, and extend lengthwise of the holder body 12 for respectively anchoring and directing the extensions 6 of the suction device 4 and cautery 2 of the surgical instruments. Each slotted channel has an angular opening at the thick common end 20 of the holder body 12 for anchoring and directing the extension 6 downwardly away from the surgeon during surgery. The angular opening has an angle of approximately 5 to 15 degrees (see FIGS. 3 and 7). This angular opening is made possible by the thick common end 20 of the holder body 12. The extensions 6 are held in a predetermined place away from a surgical area but are movable in response to manipulation of the surgical instruments. The channels 26 and 28 are angled to force direction on the emerging extensions. Each slotted channel has a beveled slit or flange 60 which leads to the channel and accommodates the extension of different diameters. The flange 60 prevents the extension from popping out of the channel. The slotted channels 26 and 28 further provide safe and speedy hose or cable detachment and reattachment to the holder body 12 should the suction device or cautery instruments fall on the floor.

Figure 11:
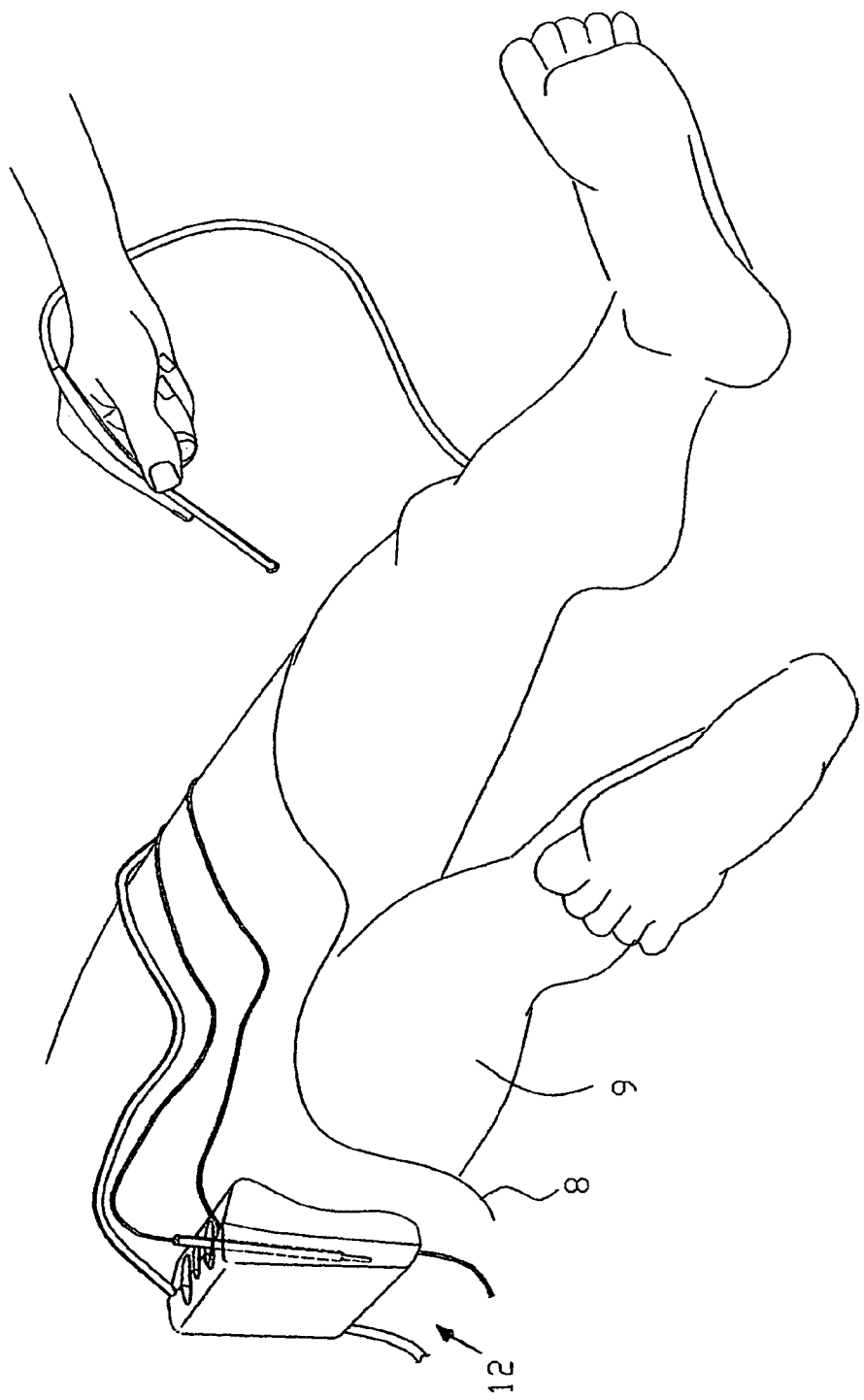
FIG. 11 is a perspective view of the present invention disposable surgical instrument apparatus attached to a surgical drape across a patient thereon.

Referring to FIGS. 1, 3, 4, 5 and 6, there is shown a pressure sensitive adhesive means 39 which includes an adhesive surface 40 covered by a removable cover 42. The pressure sensitive adhesive means 39 is affixed to the contoured bottom surface 16 of the holder body 12 adjacent to the thick common end 20. When the removable cover 42 is removed from the adhesive surface 40, the holder body 12 can be secured to a surgical drape 8 around a patient 9 (see FIG. 11). The pressure sensitive adhesive means 39 provides for secure and quick attachment to the sterile drape 8 at a site convenient to the surgeon. The apparatus 10 may be attached to the patient directly, to the drape around the patient, incorporated into the drape or even attached to a convenient stand or table adjacent to the operating room table.

Figure 2:
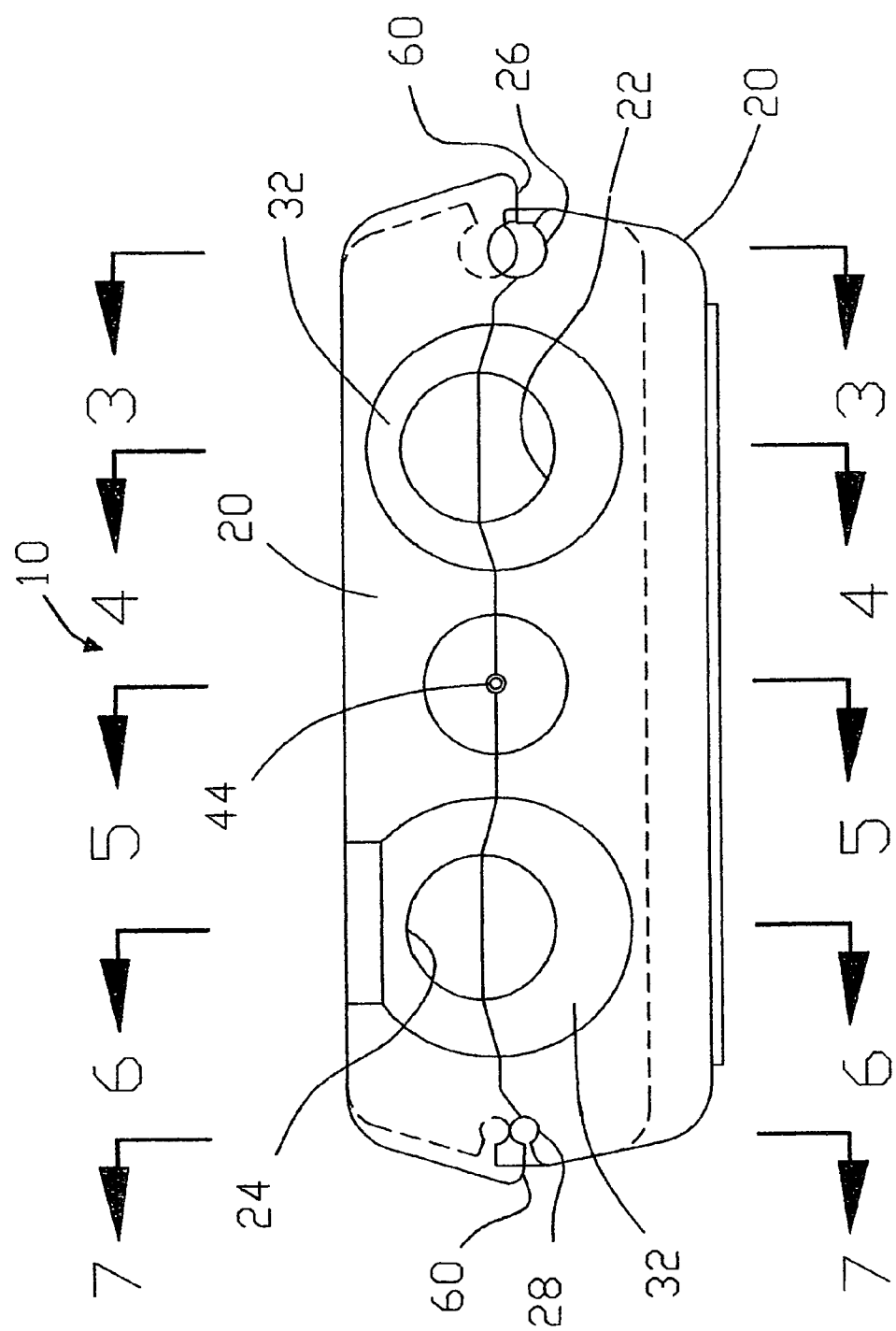
FIG. 2 is an enlarged front end plan view of the disposable surgical instrument apparatus of the present invention shown in FIG. 1.
Figure 5:
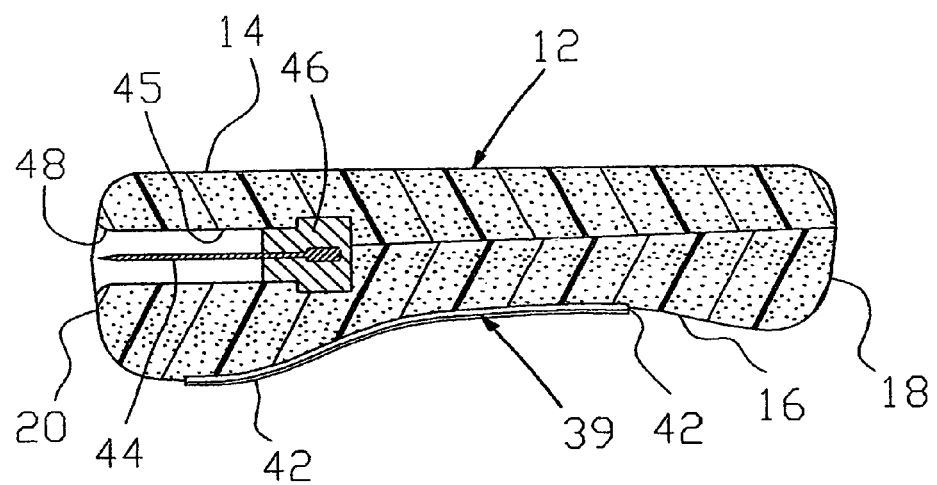
FIG. 5 is a cross-sectional view taken along line 5-5 of FIG. 2.

Referring to FIGS. 2, 5 and 9A, there is shown a cleaning means 43 which includes a cleaning spike or pin 44 attached to a butt insert 46. The butt insert 46 can be press-fitted or integrally molded within a narrow chamber 45 of the holder body 12. The cleaning spike 44 is used for dislodging clogged soft tissue or bone fragments from the suction nozzle. The narrow chamber 45 is located parallel and between the two elongated cylinders 22 and 24. The chamber 45 has a conical opening 48 at the common end 20 of the holder body 12 for ease of insertion of the suction nozzle of the suction device 4, such that the suction nozzle of the suction device can be inserted into the cleaning spike 44 for prying and cleaning loose obstructions in the suction nozzle of the suction device 4. The cleaning spike 44 can be made of metal material as shown in FIG. 9A. The components of the cleaning means 143 can be integrally molded into a one-piece plastic component which includes a cleaning spike 144 and a butt insert 146 as shown in FIG. 9B.

Referring to FIGS. 1 and 8, there is shown a small abrasive pad 50 which is affixed on the top surface 14 of the holder body 12 of the apparatus 10 for cleaning a tip of the cautery 2 and scraping char off the tip of the cautery. This abrasive pad 50 provides more efficient means for removing the char from the active cautery electrode tip. The abrasive pad 50 has two abrasive surfaces 52 at an angle to each other for cleaning the tip of the cautery.

Figure 12:
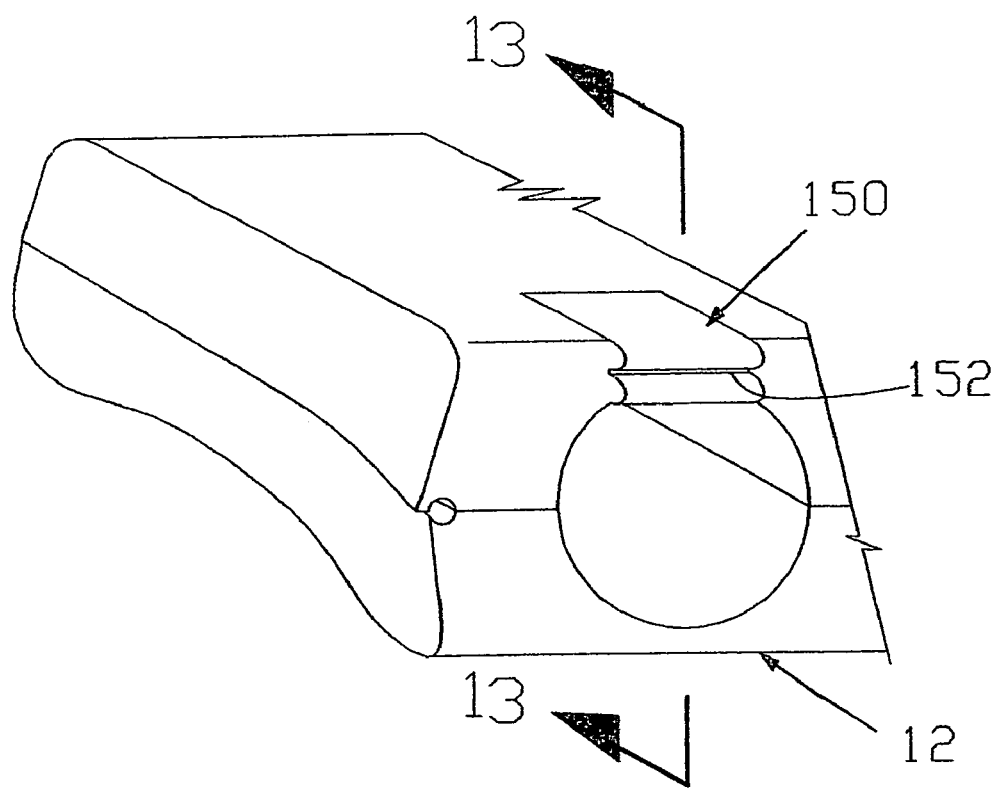
FIG. 12 is a partial perspective view of an abrasive pad attached to the holder body of the present invention disposable surgical instrument apparatus.
Figure 13:
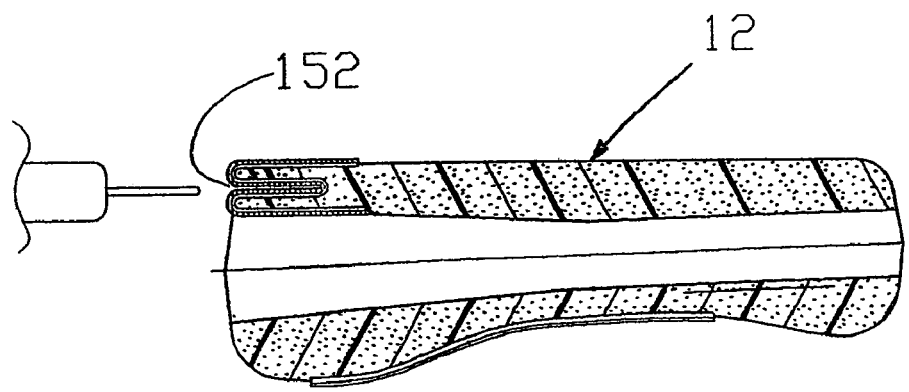
FIG. 13 is a cross-sectional view taken along line 13-13 of FIG. 12.

Referring to FIGS. 12 and 13, there is show an alternative abrasive pad 150 which is integrally mounted to the holder body 12 and a slit 152 which is formed to allow the insertion of the tip of cautery to be cleaned in one motion.

Figure 14:
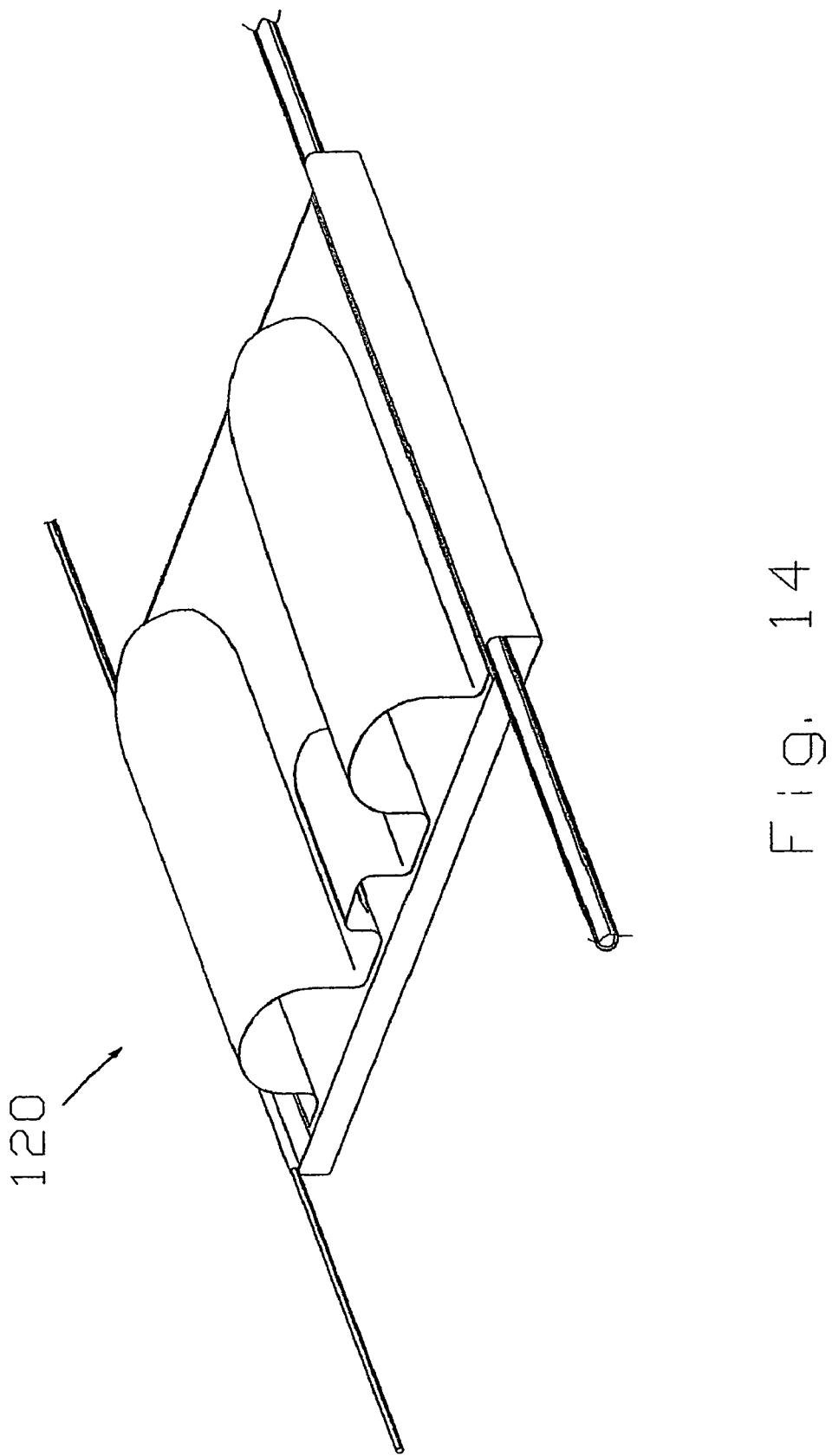
FIG. 14 shows an alternative construction of the disposable surgical instrument apparatus in accordance with the present invention.

Referring to FIG. 14, there is shown an alternative method of constructing the present invention disposable surgical instrument holder and cleaner apparatus 110. The method is vacuum formed from vinyl urethane.

What is provided by the present invention is a secure, sterile, light-weight, flame-retardant, non-conducting, non-toxic apparatus, which converts the generally irregular, convex, unusable, unstable surface over a draped surgical patient into a usable, stable, working space for the surgeon. The entire apparatus 10 can be discarded at the end of the operation.

The apparatus 10 may be constructed from a generally block of flexible semi-rigid foam material. The foam walls of the apparatus 10 provide physical, electrical and thermal insulation from the patient. It will be appreciated that the present invention is not limited to the flexible foam material. It is emphasized that while the flexible foam material is preferred, it is also within the spirit and scope of the present invention to use other materials, such as plastic foam material, urethane material, cross-linked polyethylene foam material or any other suitable material. The apparatus 10 is being conveniently package sterile in a strippable sterile package.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. The above specification, examples and data provide a complete description of the manufacture and use of the composition of the invention. Since many embodiments of the invention can be made without departing form the spirit and scope of the invention, the invention resides in the claims hereinafter appended.

What is claimed is:

1. An apparatus for holding at least one surgical instrument used in a surgery, comprising:
   (a) a holder body having a top surface, a contoured bottom surface and at least one elongated cylinder sized to hold said at least one surgical instrument when not in use during surgery, but allow easy removal of said at least one surgical instrument;

(b) at least one elongated open slotted channel located adjacent to said at least one elongated cylinder for anchoring and directing a hose or a cable of said at least one surgical instrument and is held in a predetermined place away from a surgical area but is movable in response to manipulation of the at least one surgical instrument so as not to restrain movement of the at least one surgical instrument;

(c) a cleaning spike located within a narrow chamber of said holder body and located parallel to said at least one elongated cylinder for prying and cleaning loose obstructions in said at least one surgical instrument;

(d) an abrasive pad located on said top surface of said holder body and having two abrasive surfaces at an angle to each other for cleaning a tip of said at least one surgical instrument;

(e) said at least one elongated cylinder further having a sealed chamber with a passageway decreasing diameter for accommodating a plurality of different size suction nozzles and stopping the suction action and muffling the noise from the suction nozzle of a suction device of said at least one surgical instrument; and (f) pressure sensitive adhesive having an adhesive surface covered by a removable cover for securing said contoured bottom surface of said holder body to a surgical drape around a patient.

2. The apparatus in accordance with claim 1 wherein said holder body is made of flexible foam material.

3. The apparatus in accordance with claim 1 wherein said holder body is made of urethane material.

4. The apparatus in accordance with claim 1 wherein said holder body is disposable.

5. An apparatus for holding at least two surgical instruments used in a surgery, comprising:

(a) a holder body made of foam material and having a top surface, a contoured bottom surface and at least two elongated cylinders disposed adjacent one another, each elongated cylinder having an open end at a common end of the holder body and sized to hold said at least two surgical instruments when not in use during surgery, but allow easy removal of said at least two surgical instruments;

(b) one of said at least two elongated cylinders having a sealed chamber with a passageway decreasing in diameter for accommodating a plurality of different size suction nozzles and stopping the suction action and muffling the noise from the suction nozzle of a suction device of said at least two surgical instruments;

(c) at least two elongated open slotted channels located adjacent to said at least two elongated cylinders respectively for anchoring and directing a hose of said suction device and a cable of a cautery of said at least two surgical instruments and are held in a predetermined place away from a surgical area but is movable in response to manipulation of the surgical instruments so as not to restrain movement of the surgical instruments;

(d) a cleaning spike located within a narrow chamber of said holder body and located parallel and between said at least two elongated cylinders, the narrow chamber having a conical opening at said common end of said holder body for ease of insertion of the suction nozzle of said suction device of said at least two surgical instruments within the narrow chamber, such that the suction nozzle of said suction device is insertable into the cleaning spike for prying and cleaning loose obstructions in the suction nozzle of said suction device of said plurality of surgical instruments;

(e) an abrasive pad located on said top surface of said holder body and having two abrasive surfaces at an angle to each other for cleaning a tip of said cautery of said plurality of surgical instruments; and (f) pressure sensitive adhesive for securing said contoured bottom surface of said holder body to a surgical drape around a patient.

6. The apparatus in accordance with claim 5 wherein said holder body is disposable.

7. A disposable surgical instrument apparatus for holding and cleaning a plurality of surgical instruments used in a surgery, the apparatus comprising:

(a) a generally rectangular shaped holder body made of foam and having a top surface, a contoured bottom surface and a plurality of longitudinal elongated cylinders disposed adjacent one another, each elongated cylinder having a conical open end at a thick common end of the holder body for ease of insertion of said plurality of surgical instruments and sized to hold said plurality of surgical instruments when not in use during surgery, but allow easy removal of said plurality of surgical instruments;

(b) one of said plurality of elongated cylinders having a sealed airtight chamber with a passageway decreasing in diameter for accommodating a plurality of different size suction nozzles and stopping the suction action and muffling the noise from the suction nozzle of a suction device of said plurality of surgical instruments;

(c) a plurality of elongated open slotted channels located adjacent to said plurality of elongated cylinders respectively and extending lengthwise of said holder body, each channel has an angular opening at said thick common end of said holder body for respectively anchoring and directing a hose of said suction device and a cable of a cautery of said plurality of surgical instruments and are held in a predetermined place away from a surgical area but is movable in response to manipulation of the surgical instruments so as not to restrain movement of the surgical instruments;

(d) pressure sensitive adhesive means having an adhesive surface covered by a removably cover for securing said contoured bottom surface of said holder body to a surgical drape around a patient;

(e) cleaning means located within a narrow chamber of said holder body and located parallel and between said plurality of elongated cylinders, the narrow chamber having a conical opening at said common end of said holder body for ease of insertion of the suction nozzle of said suction device of said plurality of surgical instruments within the narrow chamber, such that the suction nozzle of said suction device is insertable over the cleaning means for prying and cleaning loose obstructions in the suction nozzle of said suction device of said plurality of surgical instruments; and (f) an abrasive pad located on said top surface of said holder body and having at least one abrasive surface for cleaning a tip of said cautery of said plurality of surgical instruments.

8. The apparatus in accordance with claim 7 wherein said cleaning means includes a cleaning spike attached to a butt insert.

9. The apparatus in accordance with claim 8 wherein said cleaning means is integrally formed.

10. A surgical instrument apparatus for holding and cleaning a plurality of surgical instruments used in a surgery, the apparatus comprising:

(a) a holder body made of foam material and having a top surface, a contoured bottom surface and a plurality of longitudinal elongated cylinders disposed adjacent one another, each elongated cylinder having a conical open end at a common end of the holder body for ease of insertion of said plurality of surgical instruments not in use and sized to hold one of said plurality of surgical instruments when not in use during surgery, but allow easy removal of said plurality of surgical instruments;

(b) one of said plurality of elongated cylinders having a sealed airtight chamber with a passageway decreasing in diameter for accommodating a plurality of different size suction nozzles and stopping the suction action and muffling the noise from the suction nozzle of a suction device of said plurality of surgical instruments;

(c) a plurality of elongated open slotted channels located adjacent to said plurality of elongated cylinders respectively and extending lengthwise of said holder body for anchoring and directing a hose of said suction device and a cable of a cautery of said plurality of surgical instruments and are held in a predetermined place away from a surgical area but is movable in response to manipulation of the surgical instruments so as not to restrain movement of the surgical instruments;

(d) an adhesive on the contoured bottom surface of said holder body;

(e) an abrasive pad located on said top surface of said holder body; and (f) a cleaning spike located within a chamber of said holder body and located parallel and between said plurality of elongated cylinders, the chamber having a conical opening at said common end of said holder body.

11. The apparatus in accordance with claim 10 wherein said holder body is disposable.

* * * * *